United States Patent
Dosmann et al.

(10) Patent No.: US 8,184,273 B2
(45) Date of Patent: May 22, 2012

(54) METHOD OF DETERMINING GLUCOSE CONCENTRATION OF A WHOLE BLOOD SAMPLE

(75) Inventors: Andrew J. Dosmann, Granger, IN (US); Christine D. Nelson, Edwardsburg, MI (US); Mary Ellen Warchal-Windham, Osceola, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 12/987,516

(22) Filed: Jan. 10, 2011

(65) Prior Publication Data

US 2011/0102768 A1 May 5, 2011

Related U.S. Application Data

(60) Continuation of application No. 12/834,639, filed on Jul. 12, 2010, now Pat. No. 7,869,009, which is a division of application No. 11/791,556, filed as application No. PCT/US2005/045233 on Dec. 12, 2005, now Pat. No. 7,787,109.

(60) Provisional application No. 60/635,666, filed on Dec. 13, 2004.

(51) Int. Cl.
   *G01N 33/48* (2006.01)
(52) U.S. Cl. ....................................................... 356/39
(58) Field of Classification Search .................. 356/39
   See application file for complete search history.

(56) References Cited

U.S. PATENT DOCUMENTS

| | | | |
|---|---|---|---|
| 4,747,687 A | 5/1988 | Hoppe et al. | |
| 5,037,199 A | 8/1991 | Hlousek | |
| 5,054,878 A | 10/1991 | Gergely et al. | |

(Continued)

FOREIGN PATENT DOCUMENTS

| | | | |
|---|---|---|---|
| EP | 0 160 768 B1 | 5/1989 | |
| EP | 0 160 708 B1 | 10/1989 | |
| EP | 0 743 514 A1 | 11/1998 | |
| EP | 0 960 946 B1 | 7/2005 | |
| WO | WO 2004/081612 A2 | 9/2004 | |

OTHER PUBLICATIONS

Written Opinion of the International Searching Authority corresponding to co-pending International Patent Application No. PCT/2005/045233, European Patent Office, dated Oct. 4, 2006, 8 pages.

(Continued)

*Primary Examiner* — Roy M Punnoose
(74) *Attorney, Agent, or Firm* — Nixon Peabody LLP

(57) ABSTRACT

A total transmission spectroscopy system for use in determining the analyte concentration in a fluid sample comprises a sample cell receiving area, a light source, a collimating lens, a first lens, a second lens, and a detector. The sample cell receiving area is adapted to receive a sample to be analyzed. The sample cell receiving area is constructed of a substantially optically clear material. The collimating lens is adapted to receive light from the light source and adapted to illuminate the sample cell receiving area with a substantially collimated beam of light. The first lens is adapted to receive regular and scattered light transmitted through the sample at a first angle of divergence. The first lens receives light having a first angle of acceptance. The first lens outputs light having a second angle of divergence. The second angle of divergence is less than the first angle of divergence. The second lens is adapted to receive light from the first lens and adapted to output a substantially collimated beam of light. The detector is adapted to measure the light output by the second lens.

16 Claims, 11 Drawing Sheets

U.S. PATENT DOCUMENTS

| | | | |
|---|---|---|---|
| 5,194,393 | A | 3/1993 | Hugl et al. |
| 5,518,689 | A | 5/1996 | Dosmann et al. |
| 5,602,647 | A | 2/1997 | Xu et al. |
| 5,611,999 | A | 3/1997 | Dosmann et al. |
| 5,866,349 | A | 2/1999 | Lilja et al. |
| 5,926,271 | A | 7/1999 | Couderc et al. |
| 6,015,969 | A | 1/2000 | Nathel et al. |
| 6,184,990 | B1 | 2/2001 | Amirkhanian et al. |
| 6,591,125 | B1 * | 7/2003 | Buse et al. ............ 600/347 |
| 6,744,502 | B2 | 6/2004 | Hoff et al. |
| 6,775,001 | B2 | 8/2004 | Friberg et al. |
| 7,740,581 | B2 * | 6/2010 | Buse et al. ............ 600/365 |
| 2002/0067481 | A1 | 6/2002 | Wolf et al. |
| 2003/0218750 | A1 | 11/2003 | Friberg et al. |

OTHER PUBLICATIONS

International Search Report corresponding to co-pending International Patent Application No. PCT/US2005/045233, European Patent Office, dated Oct. 4, 2006, 6 pages.

Extended European Search Report for EPO Application No. 08020417.5-2204 dated Apr. 28, 2009 (6 pages).

Data Preprocessing and Partial Least Squares Analysis for Reagentless Determination of Hemoglobin Concentration Using Conventional and Total Transmission Spectroscopy, Journal of Biomedical Optics (vol. 6 No. 2), Apr. 2001, 6 pages.

* cited by examiner

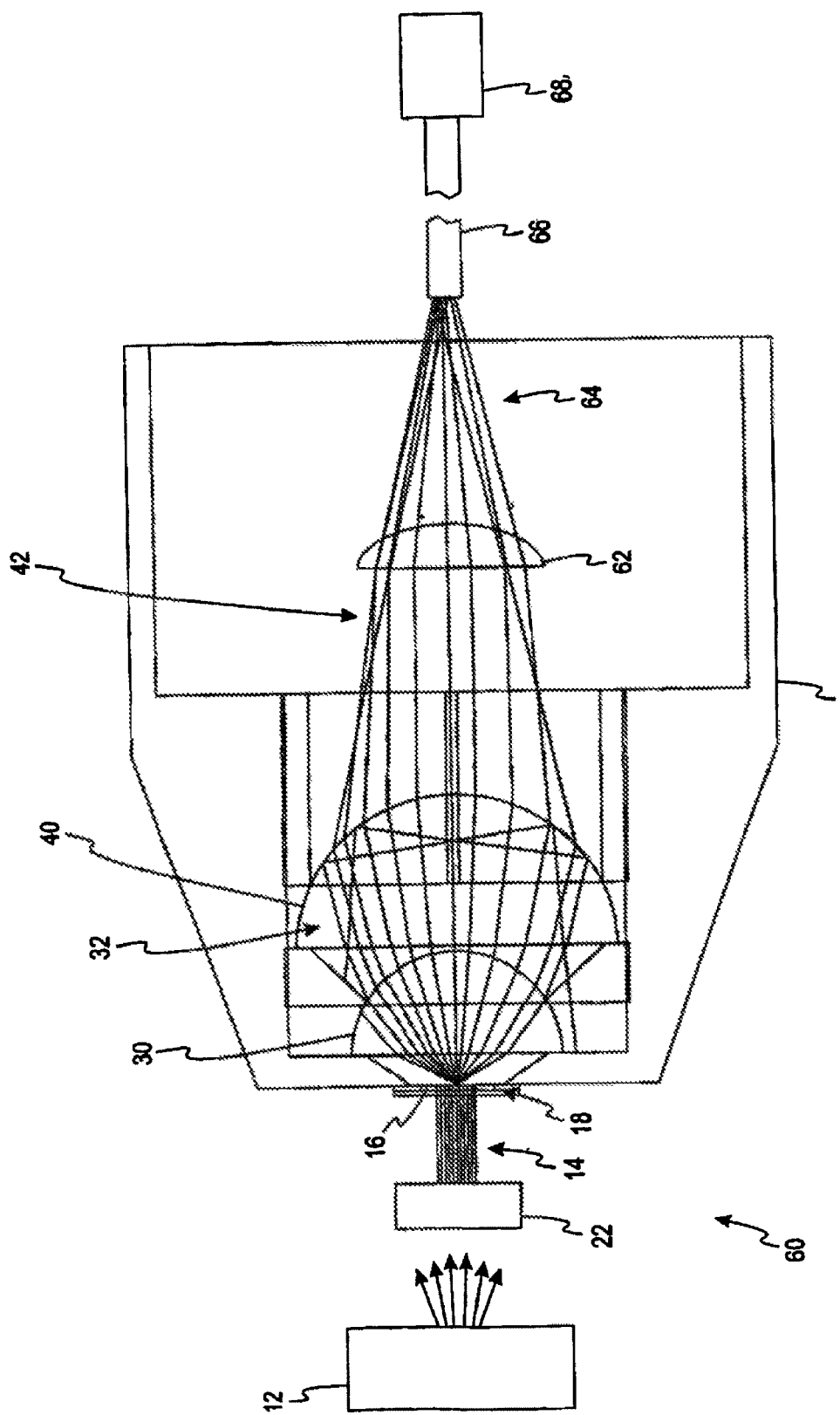

METHOD OF DETERMINING GLUCOSE CONCENTRATION OF A WHOLE BLOOD SAMPLE

CROSS-REFERENCE TO RELATED APPLICATIONS

This application is a continuation of application Ser. No. 12/834,639, filed on Jul. 12, 2010, which has been allowed; application Ser. No. 12/834,639 is a divisional of application Ser. No. 11/791,556 filed on May 23, 2007, which has issued as U.S. Pat. No. 7,787,109; application Ser. No. 11/791,556 is the national phase of Application No. PCT/US2005/045233 filed on Dec. 12, 2005, that claims priority back to Provisional Application No. 60/635,666 filed on Dec. 13, 2004.

FIELD OF THE INVENTION

The invention generally relates to spectroscopy and, more particularly, to the use of total transmission spectroscopy for determining the concentration of an analyte in body fluid.

BACKGROUND OF THE INVENTION

Transmission spectroscopy is used to perform quantitative analysis of a sample based on the transmission of a light beam through a sample contained by a sample cell. Different frequency components of the light beam are absorbed by components of the sample, whereby a frequency analysis of light transmitted through the sample permits analysis of the sample itself. Dry chemical reagents are dissolved by the sample and react with the analyte of interest to produce a chromaphoric response at certain wavelengths of light ranging from about 450 nanometers ("nm") to about 950 nm.

Transmission spectroscopy is one method for measuring the concentration of an analyte (e.g., glucose, lactate, fructosamine, hemoglobin $A_{1c}$, and cholesterol) in a body fluid (e.g., blood, plasma or serum, saliva, urine, and interstitial fluid). An indicator reagent system and an analyte in a sample of body fluid are reacted to produce a chromatic reaction— the reaction between the reagent and analyte causes the sample to change color. The degree of color change is indicative of the analyte concentration in the body fluid. The color change of the sample is evaluated, for example, using spectroscopy to measure the absorbance level of the transmitted light. Regular transmission spectroscopy is described in detail in U.S. Pat. No. 5,866,349. Diffuse reflectance and fluorescence spectroscopy is described in detail in U.S. Pat. No. 5,518,689 (entitled "Diffuse Light Reflectance Readhead"); U.S. Pat. No. 5,611,999 (entitled "Diffuse Light Reflectance Readhead"); and U.S. Pat. No. 5,194,393 (entitled "Optical Biosensor and Method of Use").

At a rudimentary level, a transmission spectroscopic analysis includes a light source that produces a beam of light for illuminating a sample and a detector for detecting light that is transmitted through the sample. The detected transmitted light is then compared to a reference sample (e.g., light from the source directly detected by the detector without the sample present). Regular transmission spectroscopy refers to the collection and analysis of the light that exits the sample at small angles (e.g., from about 0° to about) 15° relative to the normal optical axis, and not the scattered light transmitted through the sample. The normal optical axis is an axis that is perpendicular to the sample cell optical entrance and exit widows. Total transmission spectroscopy refers to the collection of substantially all of the light (including scattered light) exiting a sample at large angles (e.g., from about 0° to about) 90° relative to the normal optical axis. Existing systems for total transmission spectroscopic analysis implement an integrating sphere for collecting all of the light passing through the sample, and a required photomultiplier tube for reading the reflected light from a small portion of the inside surface of the integrating sphere.

As reported in an article entitled "Data Preprocessing and Partial Least Squares Analysis for Reagentless Determination of Hemoglobin Concentration Using Conventional and Total Transmission Spectroscopy," which appeared in the April 2001 of the Journal of Biomedical Optics (Vol. 6, No. 2), regular transmission levels (scatter excluded) of whole blood has hemoglobin concentrations ranging from about 6.6 to 17.2 g/dL are 15.8 to 0.1% T throughout the visible and near-infrared range (e.g., about 500 nm to about 800 nm) with a pathlength of only 100 µm; but, total transmission levels (scatter included) of whole blood has hemoglobin concentrations within the same range are 79% T to 2% T. The total transmission of light having a wavelength ranging from about 600 nm to about 800 nm is nearly 100% T, and there is little separation between the different hemoglobin levels. Thus, the hemoglobin concentration level has little impact on the transmitted light having a wavelength ranging from about 600 nm to about 800 nm.

A drawback associated with existing total transmission spectroscopy systems that use an integrating sphere is a low signal level that requires using a photomultiplier tube for reading the reflected light from a small portion of the inside surface of the integrating sphere. Another drawback associated with conventional total transmission spectroscopy systems is the cost of an integrating sphere and photomultiplier tube. The cost of these devices makes it cost-prohibitive to produce existing total transmission spectroscopy systems for use by a patient needing to self-test, for example, the patient's blood-glucose concentration level. As a result, spectroscopic systems for use in determining the analyte concentration in body fluids have centered on regular transmission measurements.

Existing systems using regular transmission spectroscopy also have several drawbacks. As discussed above, only the light emerging from the sample at small angles is collected using existing regular transmission spectroscopy measurements, often resulting in losing light exiting the sample at large angles. A significant portion of light scattered by the red blood cells is not collected with existing systems using regular transmission measurements, which can lead to significant loss of light resulting in very low transmission levels through whole blood.

To reduce the transmission losses using existing regular transmission systems, a reagent or detergent is typically added to the blood sample to lyse the red blood cells. Rupture of the cell walls through lysis of the blood cells reduces the scattered transmission, and increases the regular transmission of light through the sample. The addition of a lysing reagent and subsequent lysis of the red blood cells is time consuming relative to the overall measurement process. This problem is not present in existing total transmission spectroscopy methods because the scattered transmitted light and regular transmitted light is collected by the optics. Total transmission levels are typically high enough that lysing the red blood cells is not required, which significantly reduces the overall time for a chemical assay.

Another drawback associated with existing systems using regular transmission spectroscopy is a transmission bias at wavelengths of light where the chromatic reaction occurs. The indicator reagent may react with intracellular components (i.e., hemoglobin, lactate dehydogenase, etc.) released from the lysing of red blood cells causing an additional color response. The transmission bias caused by this reaction of the reagent and the certain intracellular components such as hemoglobin is not indicative of the blood-glucose level. This transmission bias causes inaccuracies in determining the analyte (e.g., glucose) concentration. The amount of bias is related to the concentration of certain cellular components in the blood cells.

Since blood lysis is not required for existing total transmission spectroscopy methods, the amount of intracellular components that may interfere with the glucose measurement is significantly reduced. Bias, however, remains for substances such as hemoglobin that absorb at visible wavelengths less than about 600 nm. It is known from the aforementioned article in the Journal of Biomedical Optics, for example, that total transmission spectra of oxy-hemoglobin has absorbance peaks at wavelengths of about 542 nm and about 577 nm. It is known that the absorbance level at wavelengths of about 542 nm or about 577 nm may be used to determine the hemoglobin concentration of the whole blood sample. The remaining interference error in glucose concentration caused by hemoglobin may be corrected for by measuring the total transmission at 542 nm or 577 nm, and correlating the absorption to known hemoglobin concentration.

The hematocrit level of whole blood may also cause a total transmission bias due to differences in the amount of scattered light at different hematocrit levels. The transmission loss caused by varying levels of hematocrit is not indicative of the blood-glucose level. Existing systems using regular transmission or total transmission spectroscopy are not capable of detecting the difference in hematocrit levels because of poor transmission level and poor separation between hematocrit levels at certain wavelengths of light.

Another drawback to existing systems using regular transmission spectroscopy is accuracy errors that result from the sample path length. A 10% variation in the path length of the sample cell area results in a 10% error in the concentration measurement for both regular and total transmission methods. The mechanical tolerance that causes the path length variation is substantially the same regardless of the path length. Existing systems using regular transmission methods, however, require a shorter path length to make up for transmission losses due to red blood cell scatter. Thus, the mechanical tolerance at a shorter pathlength results in higher concentration errors. A longer pathlength—permitted by total transmission spectroscopy systems that collect scattered light from red blood cells—reduces pathlength error.

Therefore, it would be desirable to reduce or eliminate the above described problems encountered by existing systems using regular or total transmission spectroscopy in determining analyte concentration in body fluid.

SUMMARY OF THE INVENTION

According to one embodiment, a total transmission spectroscopy system for use in determining the concentration of an analyte in a fluid sample comprises a sample cell receiving area, a light source, a collimating lens, a first lens, a second lens, and a detector. The sample cell receiving area is adapted to receive a sample to be analyzed. The sample cell receiving area is constructed of a substantially optically clear material. The collimating lens is adapted to receive light from the light source and adapted to illuminate the sample cell receiving area with a substantially collimated beam of light. The first lens is adapted to receive regular and scattered light transmitted through the sample at a first angle of divergence. The first lens receives light having a first angle of acceptance. The first lens outputs light having a second angle of divergence. The second angle of divergence is less than the first angle of divergence. The second lens is adapted to receive light from the first lens and adapted to output a substantially collimated beam of light. The detector is adapted to measure the light output by the second lens.

According to one method, the analyte concentration in a fluid sample is determined with a total transmission spectroscopy system. A sample to be analyzed is received in a sample cell receiving area of the total transmission spectroscopy system. A beam of light is outputted via a light source. The beam of light output is substantially collimated from the light source. The sample is illuminated with the substantially collimated beam of light output from the light source. Regular and scattered light transmitted through the sample is collected with a first lens. The angle of divergence of the transmitted light is reduced with the first lens. The light having a reduced angle of divergence is received with a second lens. The received light is substantially collimated with the second lens. The substantially collimated light from the second lens is measured with a detector.

According to one method, light transmitted through a fluid sample is measured with a total transmission spectroscopy system. The sample is illuminated with a substantially collimated beam of light. Regular and scattered light transmitted through the sample is collected with a first lens. The angle of divergence of the transmitted light is reduced with the first lens. The transmitted light is substantially collimated with a second lens after reducing the angle of divergence. The substantially collimated transmitted light is measured with a detector.

According to another method, the concentration of an analyte in a fluid sample is measured using a total transmission spectroscopy system. The system includes a collimated light source, a sample receiving area, a first lens being adapted to receive regular and scattered light transmitted through the sample, a second lens being adapted to receive light from the first lens and adapted to output a substantially collimated beam of light, and a detector. The sample reacts with a reagent adapted to produce a chromatic reaction in a sample cell receiving area of the system. The sample is illuminated with a substantially collimated beam of near-infrared light output by the light source of the system. The near-infrared light transmitted through the sample is measured with a detector of the system. The sample is illuminated with a substantially collimated beam of visible light output by the light source of the system. The visible light transmitted through the sample is measured with the detector. A ratio of the measured visible light to the measured near-infrared light transmitted through the sample is determined.

According to yet another method, the glucose concentration in a blood sample is determined using a total transmission spectroscopy system. The system includes a first lens adapted to receive regular and scattered light transmitted through the sample and a second lens adapted to receive light from the first lens and adapted to output a substantially collimated beam of light. The method comprises reacting the blood sample with a dried reagent to produce a chromatic reaction in a sample cell receiving area. The sample is illuminated with a substantially collimated beam of visible light output by a light source of the system. The visible light is transmitted through the sample is measured with a detector of the system. The sample is illuminated with a substantially collimated beam of near-infrared light output by the light source. The near-infrared light transmitted through the sample is measured with the detector. A correction is made for the transmission bias caused by the hematocrit level of the blood sample. The glucose concentration in the blood sample is determined.

BRIEF DESCRIPTION OF THE DRAWINGS

FIG. 1b is a side view of a total transmission spectroscopy system for use in determining the analyte concentration in body fluid according to another embodiment of the present invention.

FIG. 5 is a plot of the glucose concentration dose response of whole blood at 20%, 40%, and 60% levels of hematocrit measured with total transmission (in absorbance units) at 680 nm, obtained using the readhead of FIG. 1a.

Figure 1A:
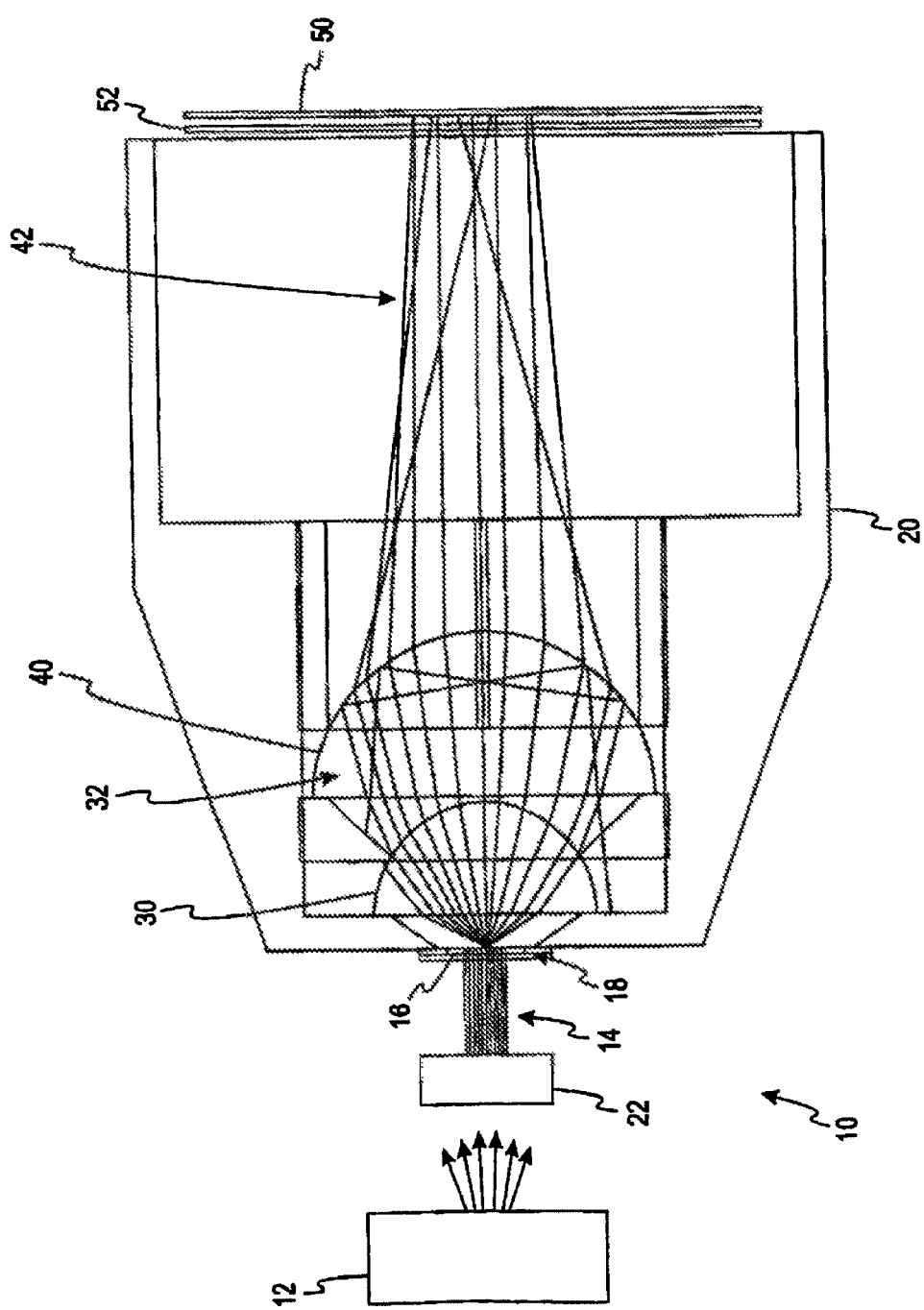
FIG. 1a is a side view of a total transmission spectroscopy system for use in determining the analyte concentration in body fluid according to one embodiment of the present invention.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF THE ILLUSTRATED EMBODIMENTS

Turning now to the drawings and first to FIG. 1a, there is shown a transmission spectroscopy system 10 implementing total transmission spectroscopy for use in the determination of an analyte concentration in a biological sample such as a body fluid. Non-limiting examples of analytes that may be determined include glucose, lactate, fructosamine, cholesterol, hemoglobin $A_{1c}$, and cholesterol. Such analytes may be in body fluids such as blood (including blood plasma and serum), saliva, urine, and interstitial fluid.

The system 10 includes a light source 12. According to one embodiment, the light source is a halogen lamp that outputs a beam of white light having a wavelength ranging from about 300 nm to about 3200 nm. According to another embodiment, the light source 12 outputs two or more beams of monochromatic light using light emitting diodes (LEDs) having center wavelengths located within a wavelength range from about 400 nm to about 1000 nm. The light output by the light source 12 is received by a collimation lens 22 that outputs a substantially collimated beam of light 14. The collimated beam of light 14 illuminates a sample 16 disposed in a sample cell receiving area 18 of a readhead 20.

According to one embodiment, the sample comprises blood with glucose that has reacted with a dry reagent system containing an indicator. According to one embodiment, a glucose-indicator reagent that may be used contains glucose dehydrogenase, NAD (nicotinamide adenine dinucleotide), diaphorase, tetrazolium indicator (WST-4) (2-benzothiazoyl-3-(4-carboxy-2-methoxyphenyl)-5-[4-(2-sulfoethylcarbamoyl)phenyl]-2H-tetrazolium), and polymers. It is contemplated that one skilled in the art may use different enzymes (such as PQQ-glucose dehydrogenase, glucose oxidase, or lactate dehydrogenase, etc.), indicators and mediators, and analytes (such as glucose, lactate, etc.). The reagent formulation does not require a hemolyzing agent to break apart red blood cells. By not breaking apart red blood cells, the total time test is faster.

The substantially collimated beam of light 14 illuminates the sample 16 and a portion of light is transmitted through the sample 16. The light that is transmitted through the sample, which comprises regular and diffusely scattered light, is collected by a first lens 30 and a second lens 40. In the illustrated embodiments, the first and second lenses are half-ball lenses. It is contemplated that other types of lens including ball lenses or aspheric lenses may be used to collect the transmitted light.

According to alternative embodiments, the first lens 30 collects light at an acceptance angle of about 72°, or a numerical aperture (NA) of about 0.951, but the acceptance angle ranges from 0° to 90° for collecting the scattered portion of the transmitted light. The light 32 exiting from the first lens 30 diverges at an angle ranging from about 15° to about 40°, and more specifically at an angle about 20°. The second lens 40 reduces the diverging light output 32 of the first lens 30 to an angle of diverging light 42 ranging from 0 to about 10 degrees, and is more specifically collimated from 0 to about 5 degrees. The regular and scattered transmitted light emerging from the sample is not diverted or scattered by the first and second lenses 30, 40. Thus, the pair of lenses 30, 40 collects substantially all of the light transmitted through the sample 16. The pair of lenses 30, 40 substantially collimates the collected light and illuminates a detector 50 with nearly normal incidence. The diverging light 42 has an angle of divergence of less than about 5°.

According to one embodiment of the spectroscopy system 10, a bandpass filter 52 or a plurality of bandpass filters may be placed before the detector 50. The bandpass filter(s) 52 typically has a center wavelength(s) of from about 400 to about 1000 nm, and a narrow bandwidth from about 5 to about 50 nm. The bandpass filter(s) 52 are typically used when a white light such as a halogen lamp is used as the light source 12. Alternatively, a bandpass filter may be used to modify the spectral bandwidth of an LED source 12, or filter out stray ambient light that does not contribute to the sample transmission. The diverging light 42 onto the bandpass filter(s) 52 is substantially collimated because light passing through the filter that is outside the filter's prescribed angle of incidence will not be within the specified bandwidth of the filter.

The first and second lenses 30, 40 combine to improve the signal level of the light guided to the detector 50 because the lenses 30, 40 collect and guide a high percentage of the light transmitted through the sample 16 to the detector 50. Further, signal level is improved by illuminating the detector 50 with a collimated beam of light that is substantially normal to the surface of the detector. Typically, the angle of divergence of the collimated beam of light is less than about 5 degrees. A normal incidence angle to the surface of the detector 50 reduces signal loss caused by Fresnel reflection off the surface of the detector 50. A significant light loss is caused by Fresnel reflection at angles of incidence greater than about 20 degrees.

The light 42 collected by the detector 50 is then compared to a reference measurement comprising a reading taken with no sample (air) in the optical path for determining the percent transmission of the sample and subsequent analyte concentration in the sample.

According to the illustrated embodiment of the spectroscopy system 10, the detector 50 and bandpass filter(s) 52 are substantially linearly aligned with the second lens 40. According to one embodiment of the present invention, the detector 50 is a silicon detector. However, other light detectors including other types of photodetectors such as lead sulfide, for example, or charged coupled devices (CCD) may be used for detecting the transmitted light. In other alternative embodiments, the detector 50 and bandpass filter(s) 52 are not linearly aligned with the second lens 40, but rather a light guide or a optical fiber(s) (not shown) having an inlet substantially linearly aligned with the second lens 40 pipes the light to a detector/filter positioned elsewhere, or to a spectrograph. The spectroscopy system 10 significantly improves the signal level obtained over existing total transmission spectroscopy systems because the light is directly coupled to the detector with the first and second lenses 30, 40.

According to one embodiment of the present invention, the path length through the sample 16 is from about 40 µm to about 200 µm and the sample has a diameter of about 1 mm. According to one embodiment, the first lens 30 is a plastic micro half-ball lens having a diameter of about 4 mm. The second collection lens 40 is a plastic micro half-ball lens having a diameter of about 8 mm. The ratio of the diameters of the first lens and the second lens is generally from about 1:2. The first and second half-ball lenses 30, 40 are constructed of acrylic according to one embodiment.

The detector 50 outputs a signal indicative of the amount of received light. According to one embodiment of the present invention, that output is monitored by a control system (not shown) of the transmission spectroscopy system 10 comprising the readhead 20 for determining when a sample has entered and filled the sample cell receiving area 18 of the readhead 20. In some embodiments of the present invention, the sample cell receiving area 18 may be part of a capillary channel, or is coupled to a capillary channel for filling the sample cell receiving area 18. The sample cell receiving area 18 is made of a substantially optically clear material according to one embodiment.

Turning now to FIG. 1b, there is shown a transmission system 60 that is used for determining an analyte concentration in a fluid sample according to another embodiment. The transmission system 60 has many of the same components that have been described above in connection with FIG. 1a. Additionally, the transmission system 60 includes a coupling lens 62 that collects the diverging light 42. The coupling lens 62 further reduces the diverging light 42 to a diverging light 64 before reaching an optical cable 66. As shown in FIG. 1b, the optical cable 66 pipes the diverging light to a spectrograph 68. In another embodiment, the spectrograph may be replaced by a detector (e.g., detector 50) shown in FIG. 1a. In such an embodiment, a filter may be added such as (e.g., filter(s) 52) described above in connection with FIG. 1a.

To prevent or inhibit errors associated with (a) underfilling the sample cell receiving area 18, or (b) timing, a control system monitors the output of the detector, which changes as the sample cell receiving area 18 fills with a body fluid (e.g., blood). A timing sequence, an embodiment of which is described in connection with FIG. 2a, allows sufficient time for the reaction between the reagent and the analyte in the sample to occur. This improves the overall performance of the testing because substantially precise timing may result in a faster and more reliable analyte determination.

Underfilling occurs, for example, when too little sample is collected to react with the predetermined amount of reagent placed in the sample cell receiving area 18. Once transmitted light is detected indicative of a filled sample cell receiving area 18, the control system knows the subsequent output of the detector 50 may be used for determining the analyte concentration in the body fluid sample (e.g., blood sample).

Additionally, according to one process of the present invention, once the detector 50 detects a sample, or a specific sample amount, the system 10 initiates a timing sequence at the conclusion of which the detector 50 begins to detect light transmitted through the sample for analysis. According to this process, the transmission spectroscopy system 10 described in connection with FIG. 2a begins with monitoring the sample area to determine the correct time for initiating the transmitted-light collection by the detector 50. At step 122, the empty sample receiving cell area 18 (FIG. 1a) is illuminated with light from the light source 12. When no sample is present in the sample receiving area, the transmission level through the system 10 is very high (e.g., nearly 100%). At step 124, the sample is input to the sample cell receiving area 18. According to one embodiment of the present invention, the reagent to be mixed with the sample has already been dried in placed in the sample cell receiving area 18. Alternatively, the reagent may be deposited with the sample or after the sample has been received in the sample cell receiving area 18.

Figure 2A:
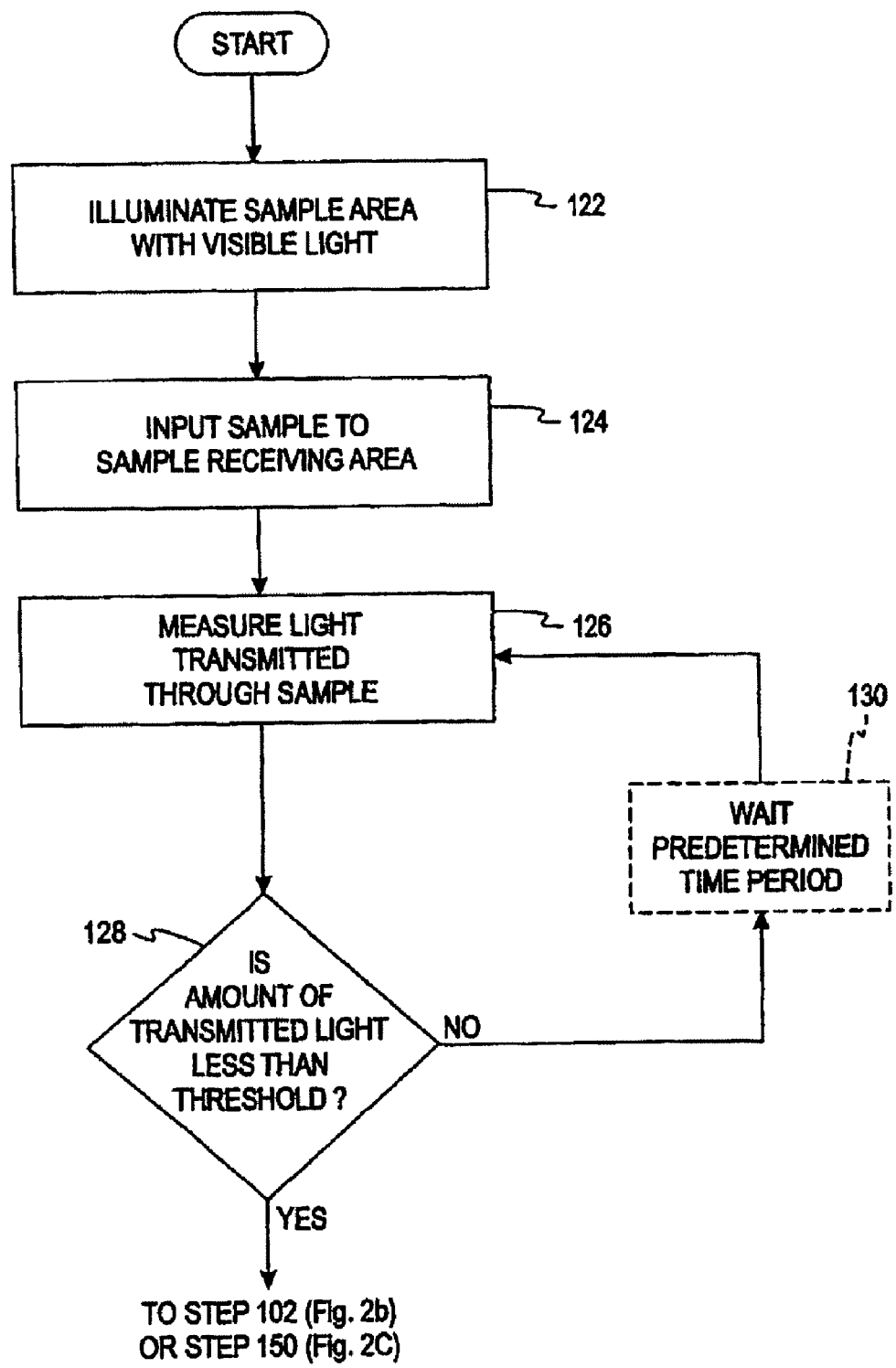
FIG. 2a is a flow chart illustrating the operation of the system of FIG. 1a according to one embodiment of the present invention that includes an underfill detection for determining if there is an adequate sample size.

The system 10 monitors the sample cell receiving area 18 by measuring the light transmitted through the sample at step 126. The system 10 compares the amount of transmitted light measured by the detector 50 to a threshold stored in a memory of the system 10 at step 128. If the measured amount of light exceeds the threshold, the system determines that a requisite amount of sample has not been input to the sample cell receiving area at step 128, and the amount of light transmitted through the sample cell receiving area 18 is re-measured at step 126. The system 10 may wait a predetermined amount of time (e.g., 5 or 10 seconds) at step 130 before taking the next measurement. If the measured amount of light is less than the threshold stored in memory, the system then may begin the analysis at step 150 (FIG. 2b) or step 102 (FIG. 2c).

While measuring the transmitted light at step 126 has been illustrated as occurring after inputting the sample to the sample receiving area, this step may be performed in a continuous manner. For example, the detector may continuously detect light transmitted through the sample cell receiving area 18 for purposes of determining when to begin the analysis set forth in FIG. 2c from the moment the system 10 has started-up to when a positive determination at step 128 occurs. Additionally, the system 10 may generate an error signal if a positive determination has not been made after a sample is input to the sample cell receiving area at step 124 (e.g., too little sample input after the system 10 has been started) according to an alternative embodiment. Additionally, it is desirable to know exactly when the reaction begins occurring to accurately determine the reaction time of the assay. The precise time for the start of the reaction may be determined by using the monitoring method of FIG. 2a.

The total transmission spectroscopy system is adapted to collect a substantially improved amount of transmitted light in the visible range (e.g., from about 400 to about 700 nm) and in the near-infrared range (e.g., from about 700 to about 1100 nm) over regular transmission systems for determining the analyte concentration in a sample. The transmission spectroscopy system 10 provides performance advantages over existing total transmission systems because a high percentage of the collected transmitted light illuminates the detector. This improved collection capability permits the system 10 to collect light in these two regions, which are used in correcting for the bias or interference caused by scatter due to different hematocrit levels (FIG. 2b) or the presence of both hemoglobin (FIG. 2c) and hematocrit (FIG. 2c) in a body fluid such as a whole blood sample.

Figure 2B:
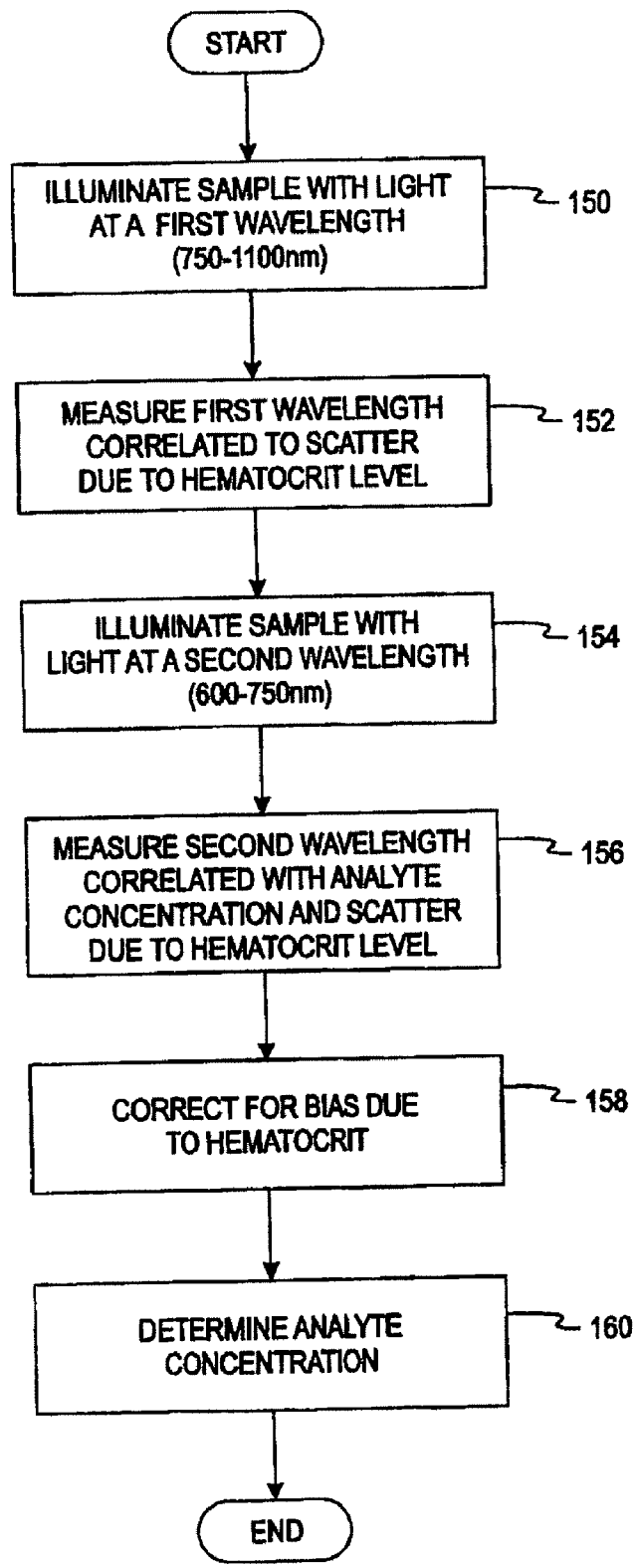
FIG. 2b is a flow chart illustrating the operation of the system of FIG. 1a according to a further embodiment of the present invention that is capable of correcting for transmission bias caused by hematocrit levels in the blood sample.
Figure 2C:
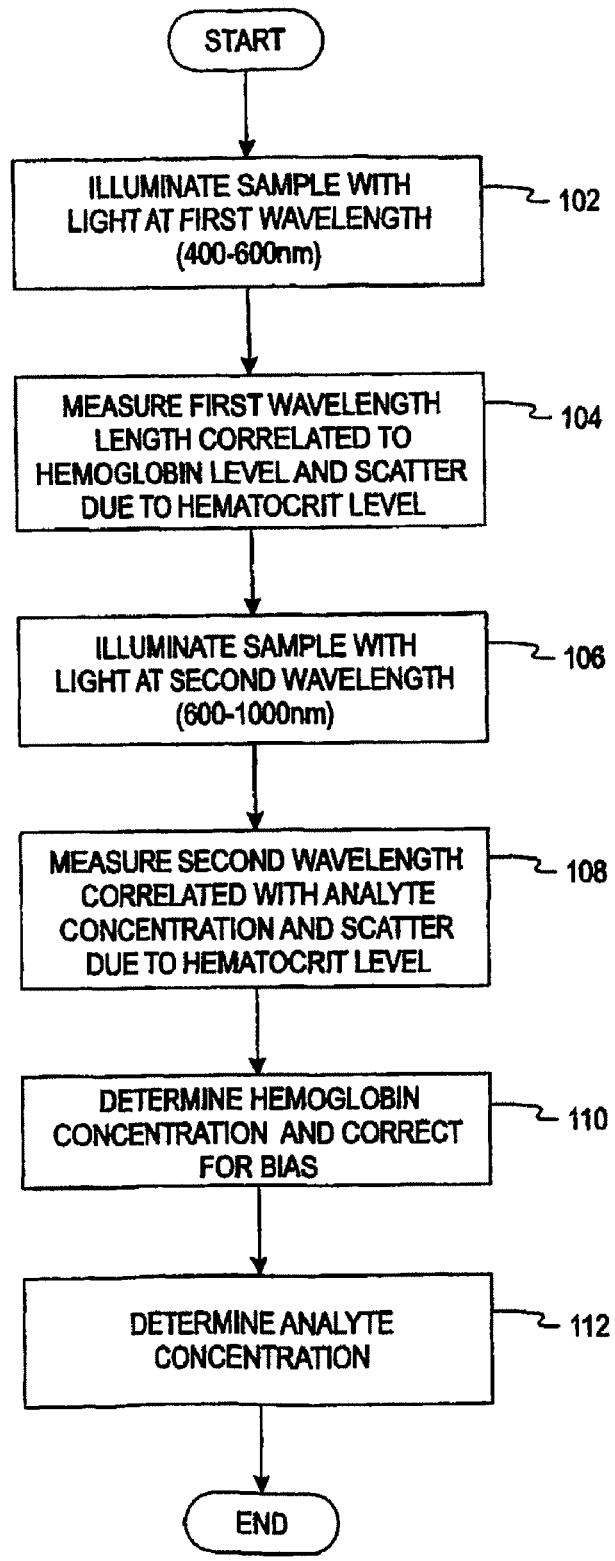
FIG. 2c is a flow chart illustrating the operation of the system of FIG. 1a according to another embodiment of the present invention that is capable of correcting for transmission bias caused by hemoglobin in a blood sample.

Referring now to FIG. 2b, one method of using the transmission spectroscopy system 10 to determine the analyte concentration in a body fluid (e.g., a whole blood sample) and to correct for the transmission biases caused by different hematocrit levels is shown. The degree of bias is a function of the hematocrit level in the whole blood sample. The indicator reagents are designed to produce chromatic reactions indicative of the blood sample's analyte concentration levels at visible light wavelengths less than about 750 nm according to one embodiment of the present invention.

In experimenting with the total transmission system 10 of FIG. 1a, it is believed that the total transmitted light varies with hematocrit level when measured at visible and near IR wavelengths from about 400 to about 1100 nm. Prior to the inventors' discovery, it was commonly held that separation between hematocrit levels could not be detected with total transmitted light having wavelengths ranging from about 600 to about 1000 nm. For example, the Journal of Biomedical Optics article discussed in the Background Section shows no separation between hematocrit levels at wavelengths from about 600 to about 800 nm.

The hematocrit level of whole blood, however, does affect the spectral response throughout the visible and near IR ("infrared") light regions (e.g., 400 to 1100 nm). The light transmission varies with and is proportional to different hematocrit levels because of differences in the scattered light due to the number of red blood cells. The hematocrit transmission bias at near IR wavelengths is proportional to the hematocrit level of the blood. A comparison between FIGS. 3a and 3b also shows that the transmission of 20% hematocrit blood is 30% T higher than a 60% hematocrit blood sample throughout the tested range from about 500 to about 940 nm. The transmission measured at near-IR wavelengths, however, is not affected by changes in glucose concentration because the indicator is designed to react and produce a chromatic response at visible wavelengths (e.g., about 680 nm).

In operation, according to one process shown in FIG. 2b, a whole blood sample reacted with reagent is illuminated with a first wavelength of light (e.g., from about 750 to about 1100 nm) at step 150 for determining the scattered portion of the measured light due to hematocrit levels in the whole blood sample. The light—normal and scattered—is measured with the detector 50 at step 152 as is described above in connection with FIG. 1a. Next, the sample is illuminated with a second wavelength of light (e.g., from about 600 to about 750 nm) at step 154, and the transmitted normal and scattered light is measured with the detector 50 at step 156 for determining both the scatted light due to hematocrit level and the chromatic response due to analyte concentration. The bias due to hematocrit-dependent scattered light is corrected for at step 158 by calculating the ratio of the transmission measurements obtained at steps 156 and 152. The analyte concentration level of the whole blood sample is calculated at step 160 using the corrected transmission from step 158.

In alternative embodiments of the present invention, additional correction algorithms such as, for example, linear regression or polynomial-fit correction algorithms may be used to determine the relationship between the hematocrit level and the bias, or interference, caused by the hematocrit at the wavelength where the analyte reaction occurs.

Turning to FIG. 2c, a method of using the transmission spectroscopy system 10 to determine the analyte concentration in, for example, a whole blood sample and to correct for the transmission bias caused by the presence of hemoglobin is shown. The degree of bias is a function of the hemoglobin level in the whole blood sample and the scatter due to the presence of red blood cells. In operation, the reaction of the whole blood sample and the reagent is illuminated with light at first wavelength from about 400 to about 600 nm at step 102. For example, the first wavelength may be about 545 nm or about 577 nm. The light—regular and scattered—is measured in absorbance units with the detector 50 at step 104 as is described above in connection with FIG. 1a.

As discussed in the Background Section, the spectra of oxy-hemoglobin shows absorbance peaks at about 545 nm and about 577 nm and is not affected by reaction at these wavelengths, because the reaction is designed to be measured at, for example, a second wavelength about 750 nm. The absorbance measured at the first wavelength includes the contribution of both the hemoglobin and the scatter due to hematocrit level of blood. According to one embodiment, the indicator reagents produce a chromatic reaction indicative of the blood sample's analyte concentration level at a second wavelength greater than about 600 nm and less than about 1000 nm (visible-near infrared). The whole blood sample and the reagent are illuminated with light at second wavelength at step 106.

The bias due to the presence of the hemoglobin in the whole blood sample is corrected for at step 110 by using the measurement obtained at step 104 to correct for the bias affecting the measurement obtained at step 108. The method for correcting the bias depends on the correlation between the hemoglobin concentration and the bias of measurement 108 caused by hemoglobin. The correlation may be linear or non-linear depending on the chemistry formulation that is used in the reaction. The analyte concentration of the sample is determined in step 112 using the corrected transmission measurement from step 110.

Similar to that discussed above in connection with FIG. 2b, the method for determining the presence of an adequate sample and the start time of the reaction illustrated in FIG. 2a may also be applied to the method of FIG. 2c in another process.

As discussed above, the transmission spectroscopy system 10 of the present invention is adapted to collect a substantially improved amount of transmitted light in the visible range and in the near-IR range over regular transmission systems for determining the analyte concentration in a sample. In experimenting with the total transmission system 10 of FIG. 1a, it is believed that hematocrit level or hemoglobin may cause transmission bias at the read wavelength where a reagent indicator has a chromatic reaction. A transmission bias that is proportional to the hematocrit level occurring at first read wavelength (e.g., greater than 750 nm) may be used to correct a second read wavelength (e.g., from about 600 to 750 nm) that includes both the bias due to the hematocrit level and the chromatic reaction of the chemical indicator. Alternatively, a transmission bias that is proportional to hemoglobin occurring at a first read wavelength (e.g., less than 600 nm) may be used to correct a second read wavelength (e.g., greater than 600 nm) where the chemical indicator causes a chromatic reaction.

EXAMPLES

Figure 3A:
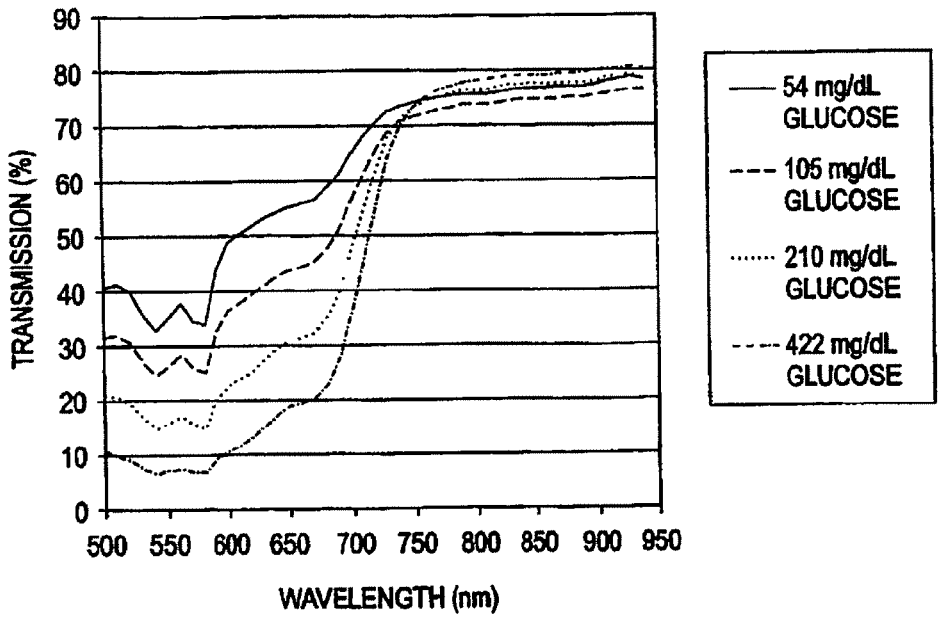
FIG. 3a is a plot of the total transmission spectra of reacted glucose assays with 20% hematocrit whole blood at 54, 105, 210, and 422 mg/dL glucose levels through the visible and near-infrared spectrum from 500 nm to 940 nm.

Referring now to FIG. 3a, one embodiment of the present invention (transmission spectroscopy system 10) measured the total transmission levels of whole blood samples having hematocrit levels of 20% reacted with reagents, and each had a different glucose concentration level—54, 104, 210, and 422 milligrams of glucose per deciliter of blood ("mg/dL glucose"). The transmission spectroscopy system 10 will be referred to in the examples as the "inventive system." White light from the light source 12 (FIG. 1a) was transmitted through the sample. The total transmission level measured from 500 nm to 940 nm was plotted in FIG. 3a for each of the glucose concentration levels. The transmission was lower from 500 to 600 nm due to the absorption of hemoglobin. Transmission loss caused by light scattered by red blood cells (hematocrit) affects the transmission from 500 nm to 940 nm. The indicator in the glucose reaction absorbs between 500 and 750 nm, so there was separation between the glucose concentration levels up to about 750 nm. As shown in FIG. 3a, at wavelengths above about 750 nm, the decrease in the total transmission level was due only to light loss from the scatter by red blood cells, so there was little separation between the samples having different glucose concentration levels.

Figure 3B:
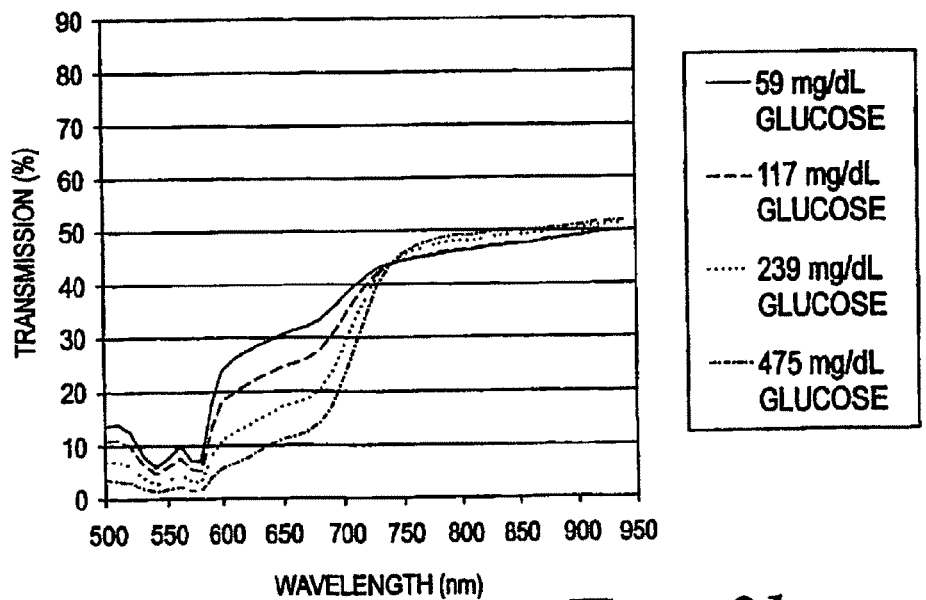
FIG. 3b is the total transmission spectra of reacted glucose assays with 60% hematocrit whole blood at 59, 117, 239, and 475 mg/dL glucose levels through the visible to near-infrared spectrum from 500 nm to 940 nm.

FIG. 3b shows that the total transmission level decreases throughout the measured wavelength range from 500 nm to 940 nm when the hematocrit level of blood is increased to 60% for blood samples having similar glucose concentrations as those plotted in FIG. 3a (59, 117, 239, and 475 mg/dL glucose). FIG. 3b also shows separation between the glucose concentration levels from 500 to about 750 nm. As shown in FIG. 3a, the transmission level about 750 nm was between 70 to 80% for the blood having a hematocrit level of about 20%. As shown in FIG. 3b, the transmission level above 750 nm was between 40 to 50% for the blood having a hematocrit level of about 60%. The differences between the spectra at 20% and 60% hematocrit were proportional for wavelengths from about 600 nm to 940 nm, above the wavelengths where there is interference due to the absorption by hemoglobin.

There, however, was little separation between the glucose concentration levels at wavelengths above 750 nm for either level of hematocrit in FIG. 3a or 3b. Thus, the 750 to 940 nm spectrum may be used to determine the level of hematocrit caused by differences in the number of red blood cells in these levels. The hematocrit level is not dependent on glucose concentration or hemoglobin at those wavelengths. The light transmission due to scattered light (determined using near-IR wavelengths) is used to correct for the interference due to hematocrit level before determining the glucose concentration level.

Figure 4A:
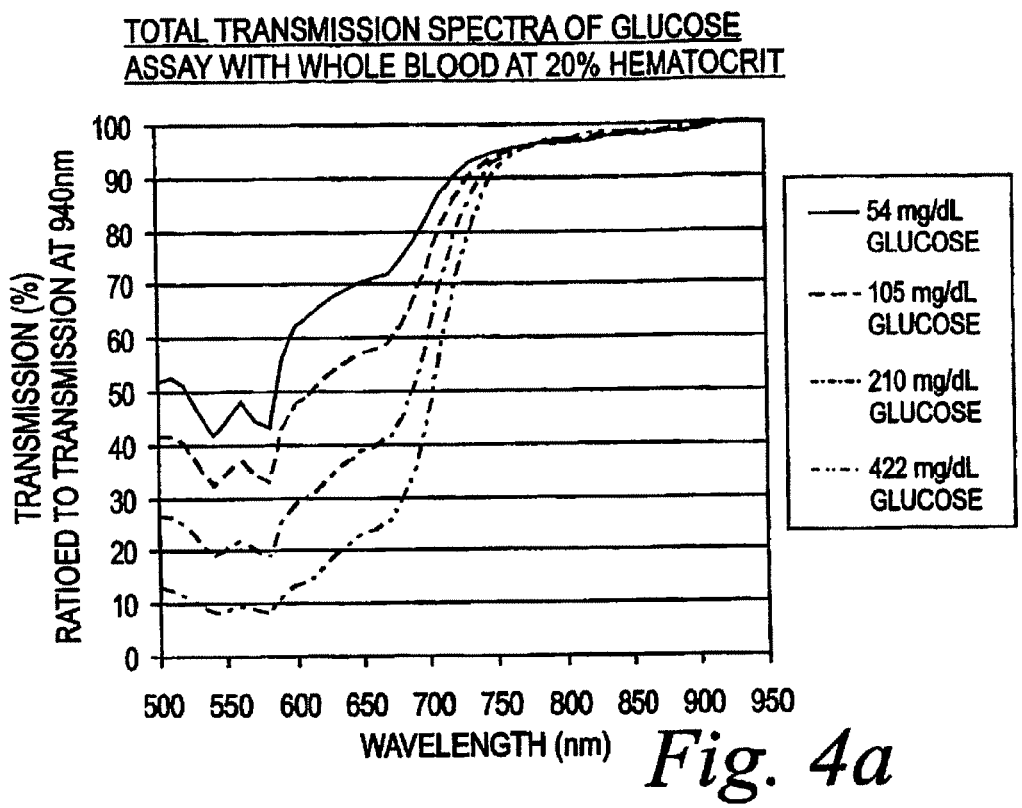
FIG. 4a is a plot of the total transmission spectra of FIG. 3a corrected for scatter by ratioing all transmission readings to the transmission at 940 nm.
Figure 4B:
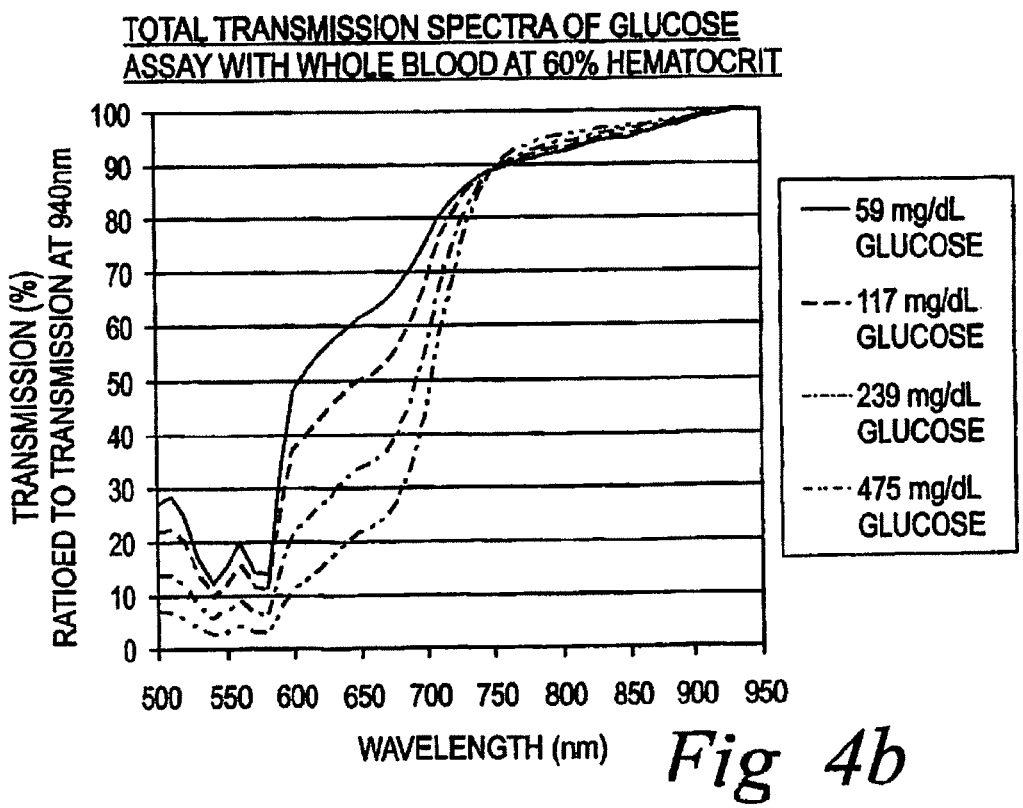
FIG. 4b is the total transmission spectra of FIG. 3b corrected for scatter by ratioing all transmission readings to the transmission at 940 nm.

FIGS. 4a, 4b show plots of the total transmission spectra of respective FIGS. 3a, 3b corrected for scatter by ratioing all transmission readings to the transmission at 940 nm. After correction, similar transmissions for similar glucose concentrations are obtained for both the 20% and 60% hematocrit blood samples in the wavelength range where the indicator reaction for the glucose assay is measured (about 660 nm to 680 nm). Thus, the near-IR wavelengths may be used to correct for differences due to hematocrit of the whole blood sample. The ability to correct for this interference error improves the accuracy of glucose concentration measurements.

Figure 5:
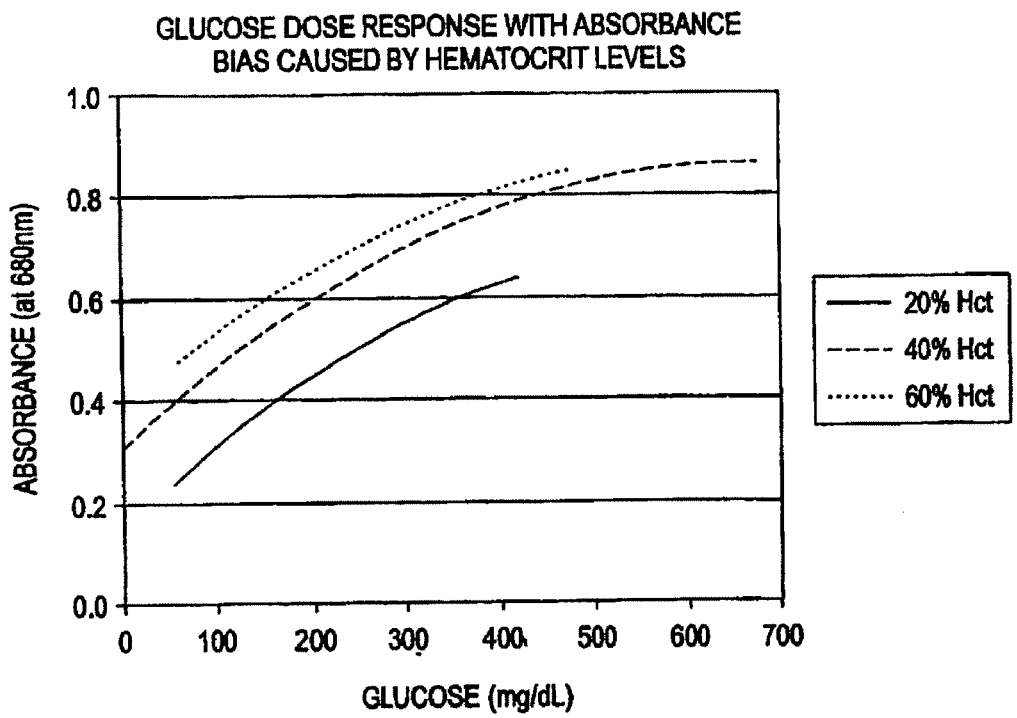

Referring now to FIG. 5, the manner in which the hematocrit level is used to correct the glucose concentration measurement is discussed according to one embodiment. The total transmission response is shown for whole blood at hematocrit levels ("Hct") of 20%, 40%, and 60% in FIG. 5, wherein the transmission (in absorbance units) for visible light having a wavelength of about 680 nm is plotted against glucose concentration level. Similar dose responses are observed at each hematocrit level, but there is a bias or interference caused by the respective hematocrit levels as shown by the separation between the three hematocrit levels plotted in FIG. 5.

Figure 6:
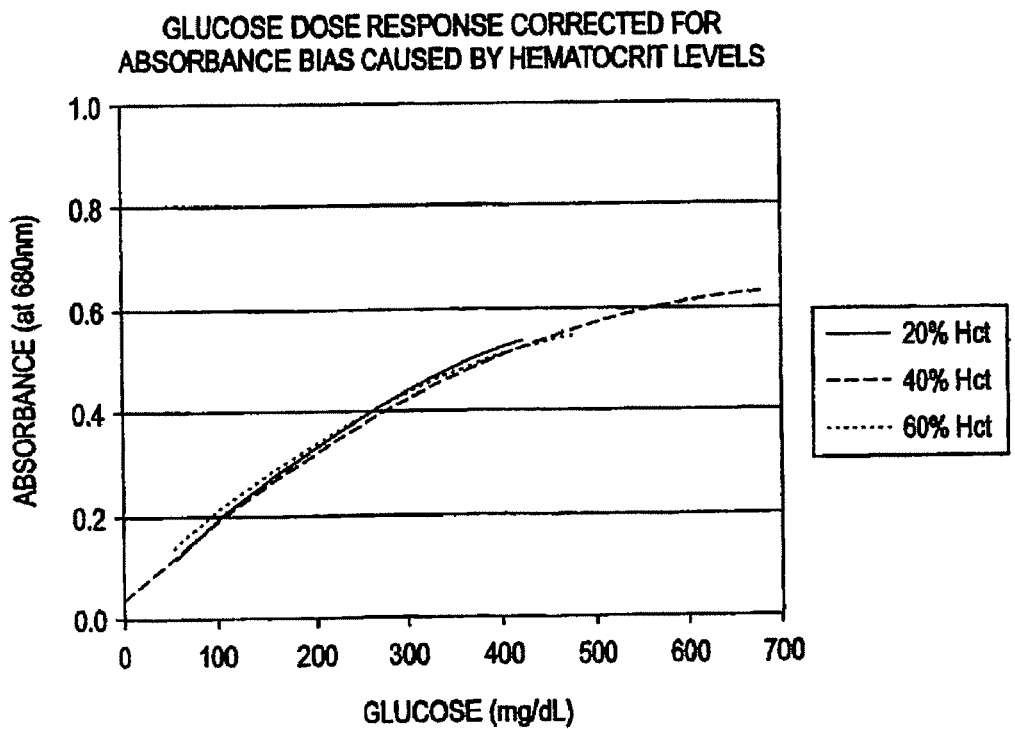
FIG. 6 is a plot of the dose response of FIG. 5 corrected for transmission bias (in absorbance units) caused by different hematocrit levels in a blood sample.

FIG. 6 shows the same data where the bias due to different hematocrit levels is corrected by a ratio of the visible light at about 680 nm divided by the near-IR light from about 750 to about 940 nm that is transmitted through a blood sample. The correction is accomplished by dividing the transmission level of the visible light at 680 nm (FIG. 5) by the transmission level of near-IR light at 940 nm for the sample as discussed above. Put simply, the hematocrit bias due to differences in scatter is "subtracted out", and FIG. 6 shows a dose response that is not affected by changes in hematocrit level.

Figure 7:
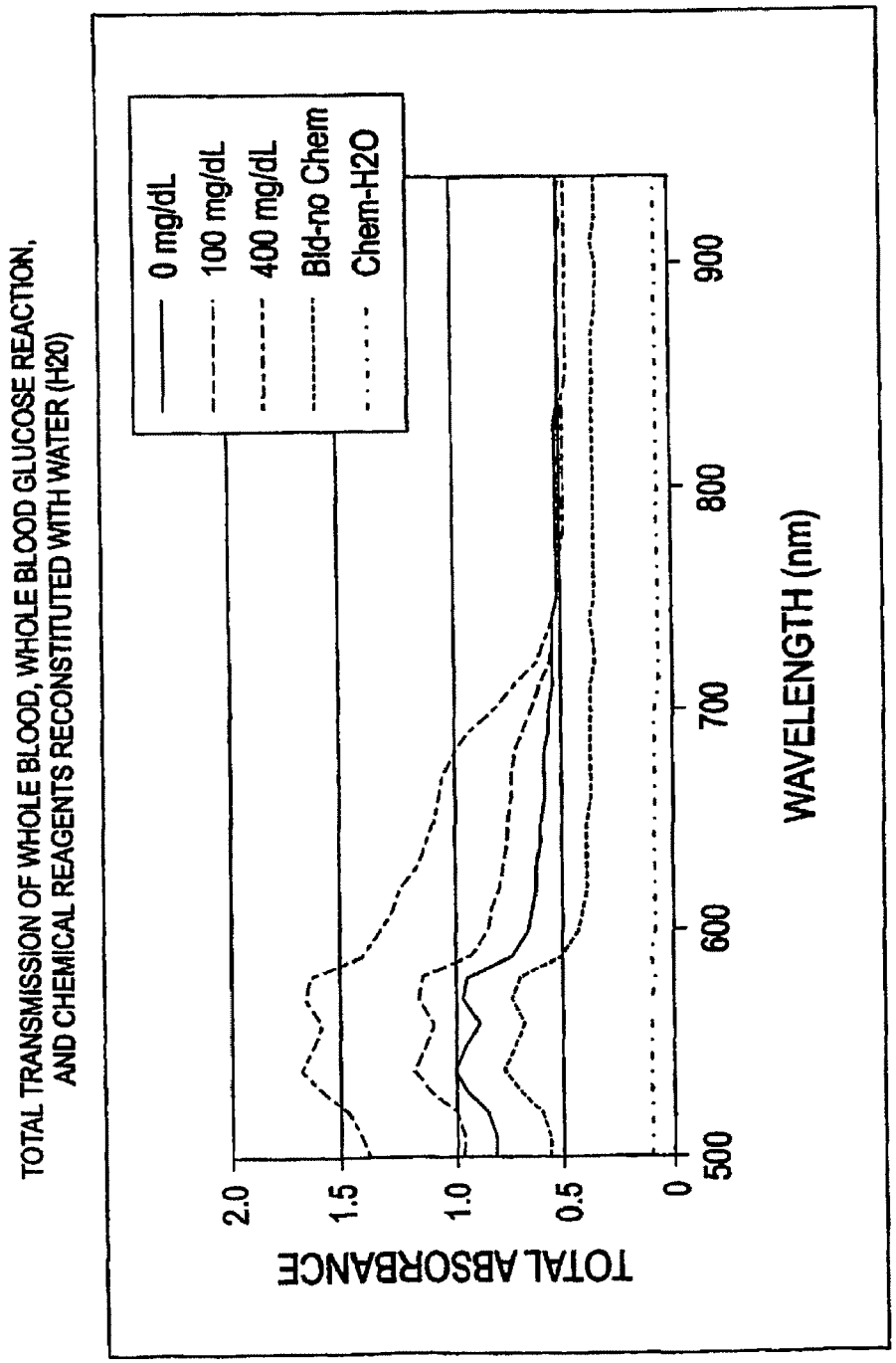
FIG. 7 is a plot of the total transmission (spectrum in absorbance units) of reagent with whole blood at 0, 100, and 400 mg/dL glucose levels, and water with reagent throughout the visible and near-infrared spectrum from 500 nm and 940 nm.

Referring now to FIG. 7, the inventive system was used to measure the glucose concentration of several samples of whole blood. Dried reagents were reconstituted with blood samples having a glucose concentration of 0, 100, and 400 mg/dL. Additionally, a 0 mg/dL blood sample with no reagent, and dried reagents reconstituted with a water sample. The blood sample without chemistry shows the spectral contribution of blood, while the water sample with reagent shows the spectral contribution of the reagent. The total absorbance levels of the reactions were recorded on a spectrograph every 5 seconds to a total test time of 60 seconds. The reaction was completed in 15 to 30 seconds. This is considerably faster than regular transmission spectroscopy, which depends on a extended reaction time of from about 60 to 90 seconds required to complete red blood cell lysis. As shown in FIG. 7, there was separation in the transmission levels of light between the various glucose concentration levels—0, 100, and 400 mg/dL—at visible wavelengths (e.g., from about 660 to about 680 nm), which are used to determine the glucose concentration levels.

Figure 8:
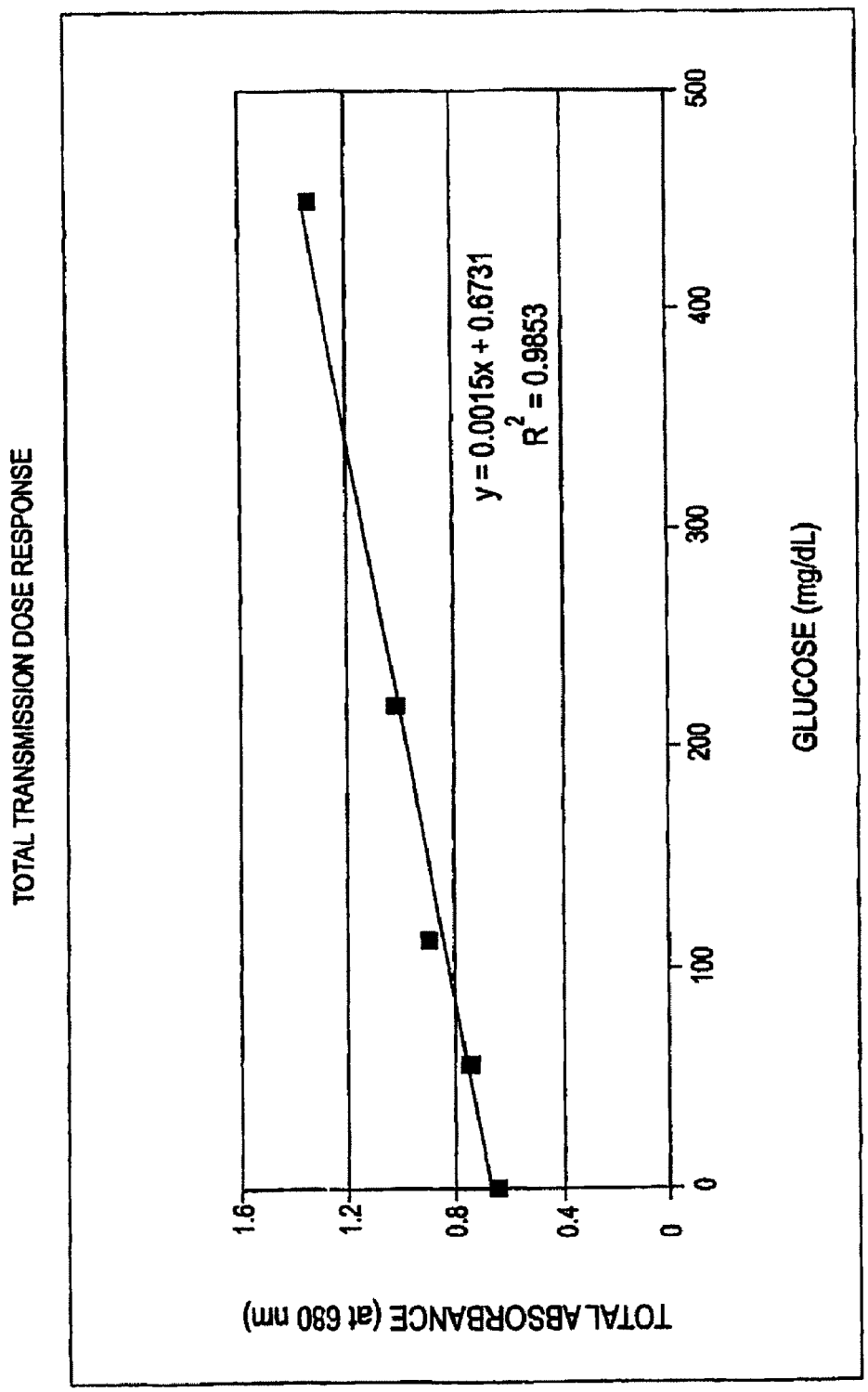
FIG. 8 plots the linear response of total transmission (in absorbance units) at 680 nm of reagent reacted with whole blood at glucose concentrations of 0, 50, 100, 200, and 450 mg/dL.

Referring now to FIG. 8, the inventive system was used to measure the 680 nm light transmitted through several whole blood samples having known glucose concentrations. In FIG. 8, the total transmitted light (plotted in absorbance units) levels were plotted against the known glucose concentration levels of the whole blood. A linear regression analysis was applied to the data plotted in FIG. 8. As shown, there is a substantially linear relationship between the amount of transmitted light and the glucose concentration. The linear correlation coefficient of 0.985 (nearly 1.000)—demonstrates that there was excellent correlation between the absorbance level and the glucose concentration using the system and method of the present invention.

Figure 9:
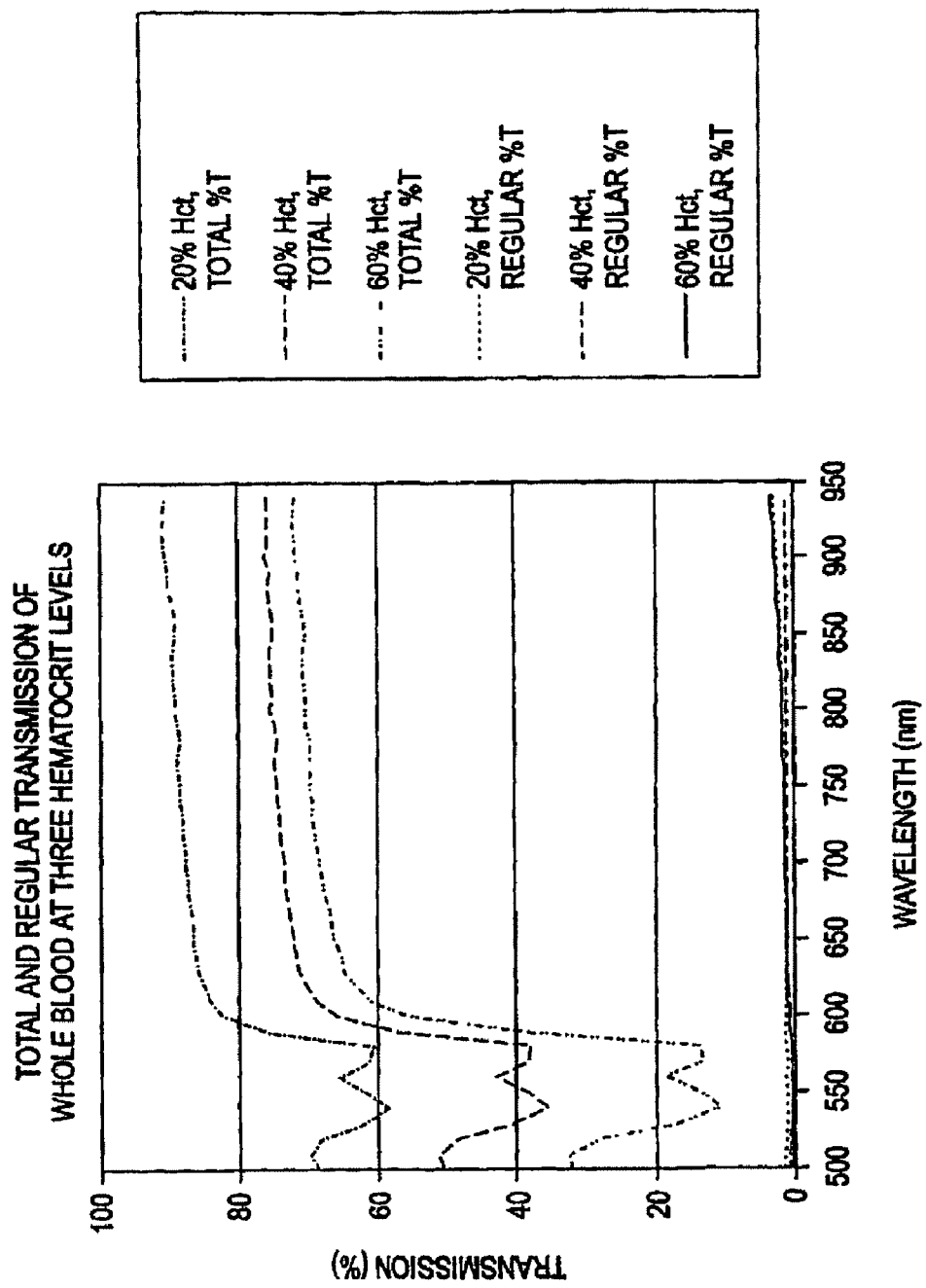
FIG. 9 shows the regular and total transmission spectrums from 500 nm to 940 nm for whole blood at 20%, 40%, and 60% levels of hematocrit.

Referring to FIG. 9, the total transmission levels for three whole blood samples having hematocrit levels of 20%, 40%, and 60%, respectively, were obtained using the inventive system. Light having wavelengths from about 500 to about 940 nm was transmitted through the whole blood samples. The pathlength of the sample receiving cell was 42 micrometers. In FIG. 9, the transmission levels for the three samples obtained were plotted against the wavelength of the transmitted light.

To illustrate the advantages of one embodiment of the inventive system over an existing spectroscopy system using a regular transmission system ("regular system"), the transmission levels for three whole blood samples having hematocrit concentration levels of 20%, 40%, and 60% are shown for both methods in FIG. 9. The regular transmission system is labeled in FIG. 9 as "% Hct, regular % T", and the total transmission system is labeled in FIG. 9 as "% Hct, Total % T". Both transmission systems used in this example illuminated the three samples with substantially collimated light having the wavelengths from about 500 to about 940 nm. The substantially collimated light, and not the scattered light, transmitted through the samples, was collected with the regular transmission system, while both regular and scattered light is collected by the inventive system. In both transmissions systems, the sample path length was about 42 µm.

Comparing the two sets of data in FIG. 9, the regular transmission level of light for the three samples is less than 2% at wavelengths greater than 500 nm. The transmission levels of light collected for the three samples obtained with the inventive system were greater than 10% T at wavelengths greater than 500 nm. Good separation between the transmission levels for the three samples obtained with the inventive system occurred for light having wavelengths of greater than 500 nm. FIG. 9 also shows that, for the data obtained with the inventive system, dips occurred in the transmission levels at from about 542 to about 577 nm. These two wavelengths of light correspond to the known absorbance peaks of oxyhemoglobin. Thus, as shown in FIG. 9, the described embodiment of the inventive system achieved a greater amount of transmitted light from 500 to 940 nm over the existing spectroscopy system using a regular transmission system, despite the absorbance of hemoglobin or the light scattered by hematocrit at these wavelengths.

In another embodiment, bias caused by scatter due to imperfections in the sample cell or small amounts of debris in the sample can be corrected in a manner similar to that for different hematocrit levels, as discussed in conjunction with in FIG. 2b. The two read wavelengths ratio corrects for contamination on the sample cell such as fingerprints, or sample cell mold defects, or scratches in the windows. This correction significantly improves assay precision compared to using one wavelength.

In another embodiment, the wavelength range where a change in absorbance verses glucose concentration occurs outside the wavelength range where hemoglobin absorbs light (e.g., wavelengths greater than about 600 nm). Use of an indicator reagent that develops at wavelengths greater than about 600 nm may also be used so that the hemoglobin absorbance peaks and the indicator reagent would not interfere with each other. FIG. 9 also shows that, for the data obtained with the inventive system, dips occurred in the transmission levels at about 530 nm and about 570 nm. These two wavelengths of light correspond to the known absorbance peaks of oxy-hemoglobin. The absorbance reading at about 542 nm or 577 nm may be used to determine the concentration of hemoglobin after subtracting out the contribution due to scatter from the red blood cells as measured in the near-IR (from about 750 to 1100 nm). In this case, the absorbance of visible light having a wavelength of about 542 nm would not change or be dependent on glucose concentration.

As discussed in the Background Section, decreasing the pathlength could increase the transmission level of the regular transmission method. The mechanical tolerances that affect the pathlength are well known to those of skilled in the art to cause a proportional error in glucose concentration. Therefore, the longer pathlength provided by the total transmission spectroscopy system of the present invention results in less glucose concentration error.

Alternate Embodiment A

A total transmission spectroscopy system for use in determining the concentration of an analyte in a fluid sample, the system comprising:

a sample cell receiving area for receiving a sample to be analyzed, the sample cell receiving area being constructed of a substantially optically clear material;

a light source;

a collimating lens being adapted to receive light from the light source and adapted to illuminate the sample cell receiving area with a substantially collimated beam of light;

a first lens being adapted to receive regular and scattered light transmitted through the sample at a first angle of divergence, the first lens receiving light having a first angle of acceptance, the first lens outputting light having a second angle of divergence, the second angle of divergence being less than the first angle of divergence;

a second lens being adapted to receive light from the first lens and adapted to output a substantially collimated beam of light; and a detector being adapted to measure the light output by the second lens.

Alternate Embodiment B

The system of Alternate Embodiment A wherein the fluid sample is blood and wherein the sample cell receiving area includes a dried reagent in the absence of a hemolyzing agent is adapted to produce a chromatic reaction when reconstituted with blood.

Alternate Embodiment C

The system of Alternate Embodiment A wherein each of the first and second lenses is a half-ball lens.

Alternate Embodiment D

The system of Alternate Embodiment A wherein the first lens has a first angle of acceptance of from 0 to about 90 degrees.

Alternate Embodiment E

The system of Alternate Embodiment A wherein the first lens has a first angle of acceptance angle greater than 70 degrees.

Alternate Embodiment F

The system of Alternate Embodiment A wherein the second angle of divergence of the first lens is from about 15 to about 40 degrees.

Alternate Embodiment G

The system of Alternate Embodiment A wherein the ratio of the diameters of the first lens to the second lens is from about 1:2.

Alternate Embodiment H

The system of Alternate Embodiment A wherein the light source outputs light having a wavelength of from about 500 to about 940 nm.

Alternate Embodiment I

The system of Alternate Embodiment A wherein the light source comprises a light-emitting diode.

Alternate Embodiment J

The system of Alternate Embodiment A wherein the light source outputs monochromatic light.

Alternate Embodiment K

The system of Alternate Embodiment A wherein the light source outputs white light.

Alternate Embodiment L

The system of Alternate Embodiment A wherein the detector comprises a silicon detector.

Alternate Embodiment M

The system of Alternate Embodiment A wherein the fluid is blood.

Alternate Embodiment N

The system of Alternate Embodiment A wherein the analyte is glucose.

Alternate Embodiment O

The system of Alternate Embodiment A wherein the first lens receives substantially all of the regular and scattered light transmitted through the sample.

Alternate Embodiment P

The system of Alternate Embodiment A further comprising a filter adapted to select a specific wavelength from the light source.

Alternate Embodiment Q

The system of Alternate Embodiment A further comprising a coupling lens and fiber optic cable for piping light from the second lens to the detector.

Alternate Embodiment R

The system of Alternate Embodiment A wherein the substantially collimated beam of light output by the second lens has an angle of divergence of less than about five degrees.

Alternate Process S

A method for use in determining the analyte concentration in a fluid sample with a total transmission spectroscopy system, the method comprising the acts of:

receiving a sample to be analyzed in a sample cell receiving area of the total transmission spectroscopy system;

outputting a beam of light via a light source;

substantially collimating the beam of light output from the light source;

illuminating the sample with the substantially collimated beam of light output from the light source;

collecting regular and scattered light transmitted through the sample with a first lens;

reducing the angle of divergence of the transmitted light with the first lens;

receiving the light having a reduced angle of divergence with a second lens;

substantially collimating the received light with the second lens; and measuring the substantially collimated light from the second lens with a detector.

Alternate Process T

The method of Alternate Process S wherein each of the first and second lenses is a half-ball lens.

Alternate Process U

The method of Alternate Process S wherein the reduced angle of divergence with the first lens is from about 15 to about 40 degrees.

Alternate Process V

The method of Alternate Process S wherein the received light with the second lens reduces the angle of divergence of the light diverging from the second lens to less than about 5 degrees.

Alternate Process W

The method of Alternate Process S wherein the light source has a wavelength from about 500 to about 940 nm.

Alternate Process X

The method of Alternate Process S wherein the light source outputs a monochromatic beam of light.

Alternate Process Y

The method of Alternate Process S wherein the light source is white light.

Alternate Process Z

The method of Alternate Process S further comprising monitoring the detector for determining when the sample cell receiving area has received a predetermined amount of sample to be analyzed.

Alternate Process AA

The method of Alternate Process Z further comprising determining the analyte concentration in the fluid sample after determining the sample cell receiving area has received a predetermined amount of sample to be analyzed.

Alternate Process BB

A method for measuring light transmitted through a fluid sample with a total transmission spectroscopy system, the method comprising the acts of:

illuminating the sample with a substantially collimated beam of light;

collecting regular and scattered light transmitted through the sample with a first lens;

reducing the angle of divergence of the transmitted light with the first lens;

substantially collimating the transmitted light with a second lens after reducing the angle of divergence; and measuring the substantially collimated transmitted light with a detector.

Alternate Process CC

The method of Alternate Process BB wherein each of the first and second lenses is a half-ball lens.

Alternate Process DD

The method of Alternate Process BB wherein reduced angle of divergence with the first lens is from about 15 to about 40 degrees.

Alternate Process EE

The method of Alternate Process BB wherein substantially collimating the received light with the second lens comprises reducing the angle of divergence of the light received with the second lens to less than about 5 degrees.

Alternate Process FF

The method of Alternate Process BB further providing a light source adapted to output a beam of light further with a wavelength of from about 500 to about 940 nm.

Alternate Process GG

The method of Alternate Process BB further providing a light source adapted to output a beam of light with a monochromatic beam of light.

Alternate Process HH

The method of Alternate Process BB further providing a light source adapted to output a beam of light of white light.

Alternate Process II

The method of Alternate Process BB wherein collecting normal and scattered light comprises collecting substantially all of the normal and scattered light transmitted through the sample.

Alternate Process JJ

The method of Alternate Process BB further comprising monitoring the detector adapted to determine when the sample cell receiving area has received a predetermined amount of sample to be analyzed.

Alternate Process KK

The method of Alternate Process JJ further comprising determining the analyte concentration in the fluid sample after determining the sample cell receiving area has received a predetermined amount of sample to be analyzed.

Alternate Process LL

A method for determining the concentration of an analyte in a fluid sample using a total transmission spectroscopy system, the system including a first lens adapted to receive regular and scattered light transmitted through the sample, a second lens adapted to receive light from the first lens and adapted to output a substantially collimated beam of light, a light source and a sample cell receiving area, the method comprising the acts of:

reacting the sample with a reagent adapted to produce a chromatic reaction in a sample cell receiving area of the system;

illuminating the sample with a substantially collimated beam of near-infrared light output by the light source of the system;

measuring the near-infrared light transmitted through the sample with a detector of the system;

illuminating the sample with a substantially collimated beam of visible light output by the light source of the system;

measuring the visible light transmitted through the sample with the detector; and determining a ratio of the measured visible light to the measured near-infrared light transmitted through the sample.

Alternate Process MM

The method of Alternate Process LL wherein the fluid sample is blood.

Alternate Process NN

The method of Alternate Process LL wherein the analyte is glucose.

Alternate Process OO

The method of Alternate Process LL wherein determining the ratio includes factoring out the transmission bias caused by the hematocrit level in the blood sample.

Alternate Process PP

The method of Alternate Process LL wherein the enzyme is glucose dehydrogenase coupled with a mediator that produces color with a tetrazolium indicator.

Alternate Process QQ

A method for determining the glucose concentration in a blood sample using a total transmission spectroscopy system, the system including a first lens adapted to receive regular and scattered light transmitted through the sample and a second lens adapted to receive light from the first lens and adapted to output a substantially collimated beam of light, the method comprising the acts of:

reacting the blood sample with a dried reagent to produce a chromatic reaction in a sample cell receiving area;

illuminating the sample with a substantially collimated beam of visible light output by a light source of the system;

measuring the visible light transmitted through the sample with a detector of the system;

illuminating the sample with a substantially collimated beam of near-infrared light output by the light source;

measuring the near-infrared light transmitted through the sample with the detector;

correcting for transmission bias caused by hematocrit level of the blood sample; and determining the glucose concentration in the blood sample.

Alternate Process RR

The method of Alternate Process QQ wherein correcting comprises determining a ratio of the measured visible light and the measured near-infrared light transmitted through the sample.

Alternate Process SS

The method of Alternate Process QQ wherein correcting comprises determining a correlation between the measured visible light and the measured the near-infrared light transmitted through the sample and applying the correlation correction to the visible light transmission measurement.

While the invention is susceptible to various modifications and alternative forms, specific embodiments are shown by way of example in the drawings and described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The invention claimed is:

1. A method of determining glucose concentration of a whole blood sample using an optical test sensor, the method comprising:

providing an optical test sensor including a reagent composition having an enzyme;

measuring transmission levels at two different wavelengths of the whole blood sample;

correcting absorbance bias of the whole blood sample, if any, caused by hematocrit levels using the transmission levels at two different wavelengths; and determining the glucose concentration using the measured transmission levels and corrected absorbance bias, if any, of the whole blood sample.

2. The method of claim 1 wherein the two different wavelengths includes a visible light wavelength and a near-IR light wavelength.

3. The method of claim 2 wherein the near-IR light wavelength is from about 700 to about 1,100 nm.

4. The method of claim 2 wherein the near-IR light wavelength is from about 750 to about 940 nm.

5. The method of claim 2 wherein the visible wavelength is from about 400 to about 700 nm.

6. The method of claim 2 wherein the visible wavelength is from about 660 to about 680 nm.

7. The method of claim 1 wherein the correction is a ratio of a measured transmission level of a visible light and a measured transmission level of a near-IR light wavelength.

8. The method of claim 7 wherein the visible wavelength is from 400 to 700 nm and the near-IR light wavelength is from 700 to 1,100 nm.

9. The method of claim 7 wherein the visible wavelength is from about 660 to about 680 nm and the near-IR light wavelength is from 700 to 1,100 nm.

10. The method of claim 7 wherein the visible wavelength is from about 660 to about 680 nm and the near-IR light wavelength is from 700 to 940 nm.

11. The method of claim 1 wherein bias due to hematocrit is within +/−10%.

12. The method of claim 1 wherein bias due to hematocrit is within +/−10% between 20% to 60% hematocrit levels.

13. The method of claim 1 wherein bias due to hematocrit is within +/−5%.

14. The method of claim 1 wherein bias due to hematocrit is within +/−10% between 20% to 60% hematocrit levels.

15. A method of determining glucose concentration of a whole blood sample using an optical test sensor, the method comprising:
- providing the optical test sensor including a reagent composition having an enzyme;
- contacting the whole blood sample with the reagent composition;
- measuring the glucose concentration of the whole blood sample;
- correcting bias of the whole blood sample, if any, caused by a hematocrit level; and
- determining the glucose concentration using the measured glucose concentration and the corrected bias, if any, of the whole blood sample wherein the bias due to the hematocrit level of the determined glucose concentration is within +/−5% between 20% to 60% hematocrit levels.

16. The method of claim 15 wherein the determined glucose concentration is between 100 and 400 mg/dL.